United States Patent [19]
Green

[11] Patent Number: 5,360,154
[45] Date of Patent: Nov. 1, 1994

[54] APPARATUS FOR CREATING PARTIAL ANASTOMOSES

[75] Inventor: David T. Green, Westport, Conn.

[73] Assignee: United States Surgical Corporation, Norwalk, Conn.

[21] Appl. No.: 915,109

[22] Filed: Jul. 17, 1992

[51] Int. Cl.⁵ .......................................... A61B 17/115
[52] U.S. Cl. ..................................... 227/179; 227/175; 227/19
[58] Field of Search ............... 227/179, 176, 175, 178, 227/113, 180, 19; 606/219; 72/393, 49, 283; 354/296, 195.1

[56] References Cited

U.S. PATENT DOCUMENTS

| | | |
|---|---|---|
| 3,995,034 | 3/1974 | Strekopytov et al. |
| 4,289,133 | 9/1981 | Rothfuss ........................... 227/179 |
| 4,470,533 | 9/1984 | Schuler ............................... 227/19 |
| 4,576,167 | 3/1986 | Noiles ............................... 227/179 |
| 4,617,928 | 10/1986 | Azfranca ............................. 227/19 |
| 4,715,520 | 12/1987 | Roehr, Jr. et al. |
| 4,915,100 | 4/1990 | Green . |
| 4,930,674 | 6/1990 | Barak . |
| 5,074,453 | 12/1991 | Tachihara et al. .................. 227/113 |
| 5,158,222 | 10/1992 | Green . |

FOREIGN PATENT DOCUMENTS

| | | | |
|---|---|---|---|
| 0190022 | 8/1986 | European Pat. Off. ............ 227/176 |
| 762869 | 3/1976 | U.S.S.R. . | |

OTHER PUBLICATIONS

Experimental Transperitoneal Laparoscopic Pyloroplasty, Pietrafitta, Joseph; Schultz, Leonard; Graber, John; Hickok, David "Surgical Laparoscopy and Endoscopy" vol. 2, pp. 104–110.

Primary Examiner—Eugenia Jones
Assistant Examiner—Allan M. Schrock

[57] ABSTRACT

An end-to-end anastomosis stapling apparatus is provided with a shroud for creating a partial anastomosis. The shroud is provided with a collar, portion for mounting the shroud onto the distal end of the stapling apparatus, and a tissue shield for shielding a predetermined portion of tissue from entering between an anvil and a staple cartridge on the stapling apparatus.

23 Claims, 6 Drawing Sheets

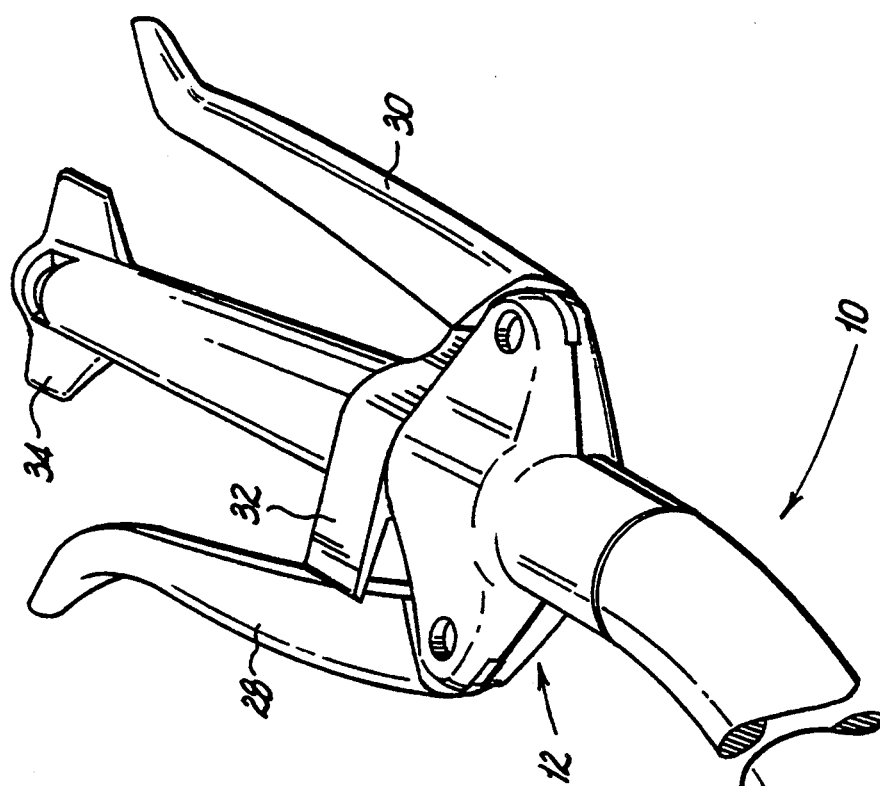
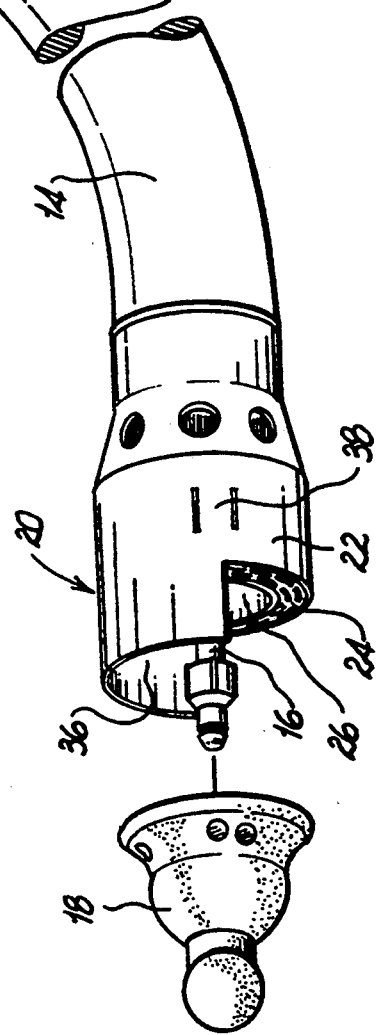
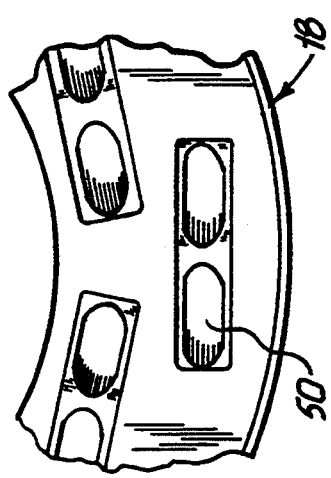
FIG.2
FIG.2A

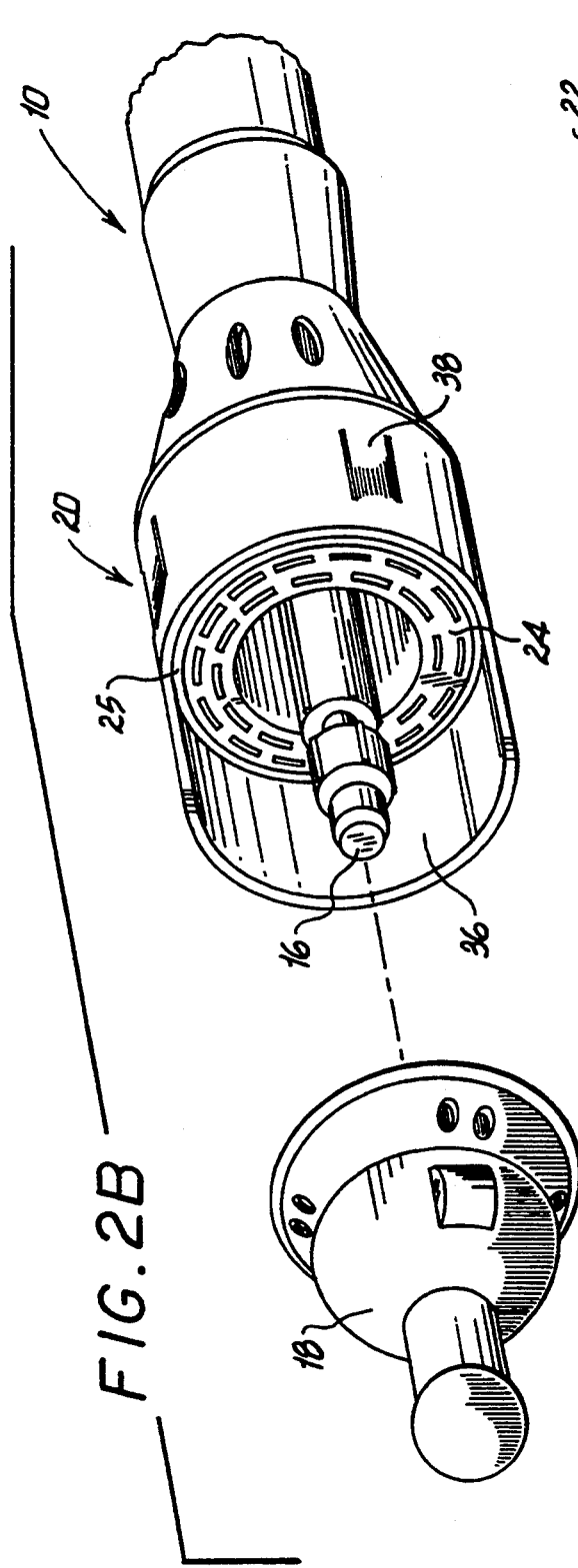
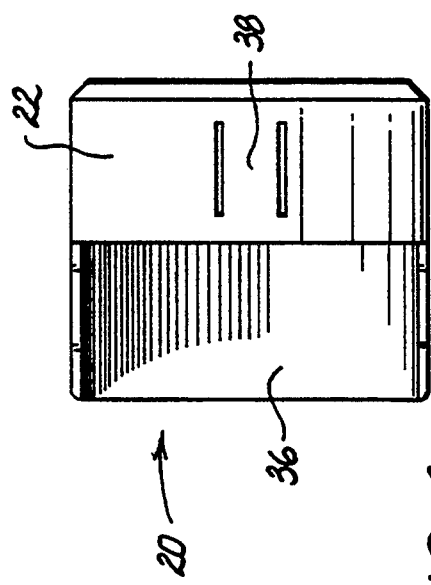
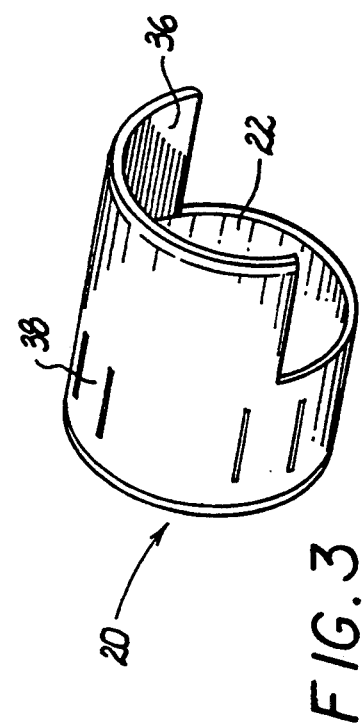

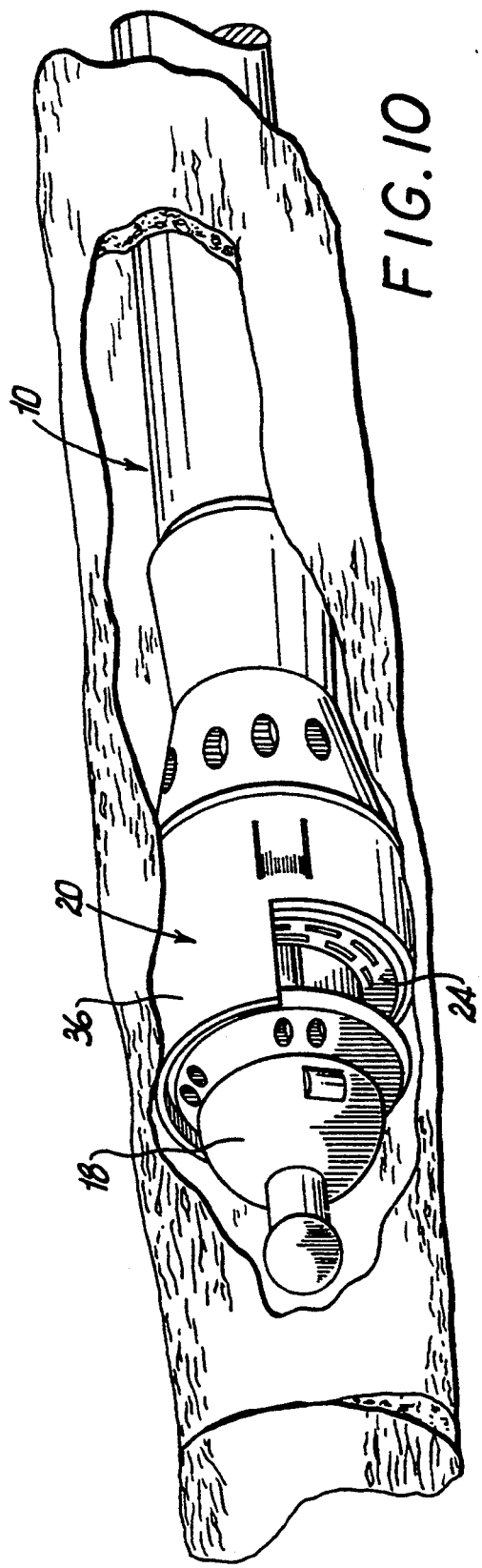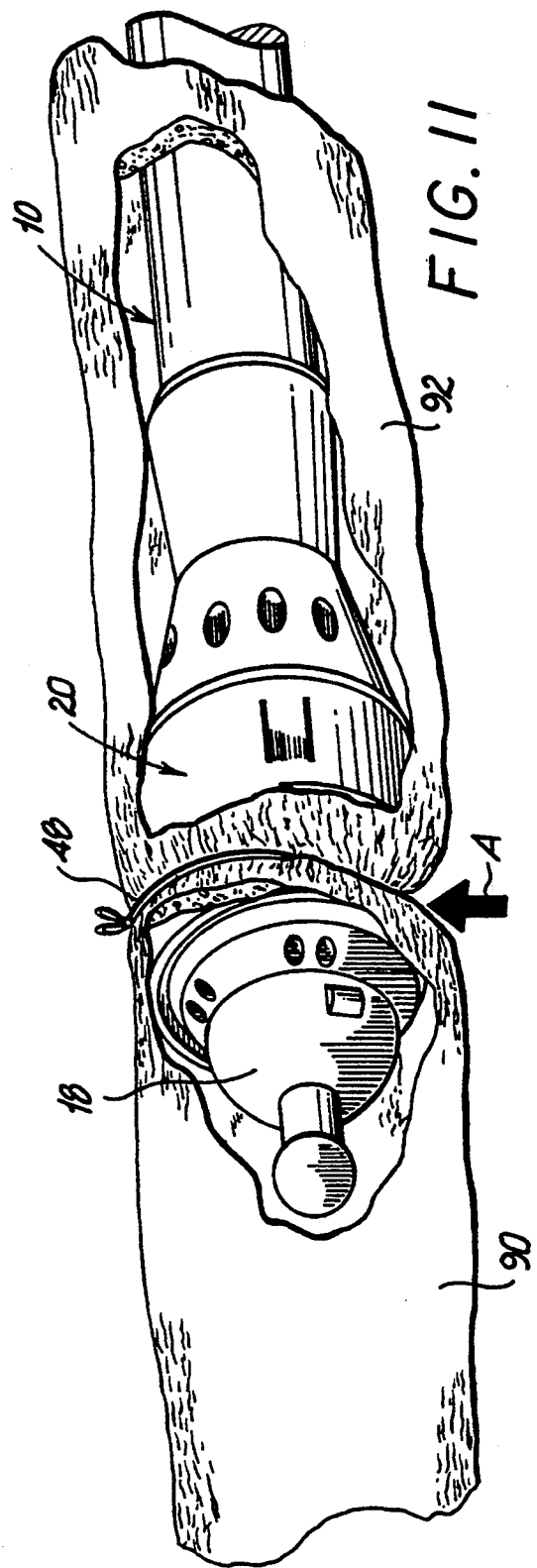

APPARATUS FOR CREATING PARTIAL ANASTOMOSES

BACKGROUND OF THE INVENTION

1. Field of the Invention

This invention relates to a circular end-to-end anastomosis stapler apparatus. More particularly, this invention relates to an apparatus for creating a partial circular anastomosis having a novel tissue shielding shroud which is adapted for detachable mounting to the stapler apparatus.

2. Description of the Related Art

Various types of surgical staplers have been known in the past for the application of staples to tissue. For example, it has been known to use various types of staplers in gastric and esophageal surgery, in both classic or modified gastric reconstructions performed end-to-end, end-to-side or side-to-side. In some cases, it has been known to create an anastomosis utilizing an instrument such as the PREMIUM CEEA TM instrument manufactured by United States Surgical Corporation or like instruments where an anvil assembly can be mounted on the end of a central rod which can be retracted within a tubular housing of the instrument. Such an instrument can be introduced into the tureen of a stomach or tubular tissue structure without the anvil in place. Thereafter, the tip of the center rod is passed through an opening which has been made near the anastomotic site so that the anvil can then be mounted on the end of the rod. Subsequently, the anvil can be inserted into the lumen and the end of the lumen tied off, for example, by a purse string suture. Thereafter, the instrument is activated in order to form the staples so as to join the ends of the lumen together. As is known, the instrument can then be removed through the opening originally made in the lumen.

It may be necessary or desirable, however, during certain circular anastomoses to effectuate a less than 360° closure. It is known to mask a potion of an array of staples from engaging tissue. An example of such a device is the subject of U.S. Pat. No. 4,470,533 to Schuler which discloses staple masking means for use with a linear stapling device. It is also known in the art to provide an arcuate or semi-circular array of staples. U.S. Pat. No. 4,617,928 to Alfranca discloses such an array of staples formed by an arcuate staple cartridge and corresponding anvil. Other partial arrays of staples are disclosed in "Experimental Transperitoneal Laparoscopic Pyloroplasty", *Surgical Laparoscopy & Endoscopy*, Vol. 2, No. 2, June 1992, pp. 104–110. These devices, however, require different size staple cartridges and knives be provided depending on the staple array desired. A need, therefore, still exists for a circular anastomosis stapler capable of performing a partial, i.e., less than 360° anastomosis without requiring additional staple cartridges or knife blades. The novel surgical apparatus according to the present invention obviates the disadvantages encountered in the prior art and provides a precise instrument which is easy to manufacture and efficient to use. The device also eliminates the need for complicated calculation of how many staples are required for the desired completed staple array and fitting the stapling device with the appropriate staple cartridge. Additionally, tissue, not desired to be stapled, is prevented, by the device of the present invention, from entering in between the staple cartridge and the anvil.

SUMMARY OF THE INVENTION

Briefly, the invention relates to a surgical fastener apparatus which includes a tubular housing, a staple cartridge mounted in the distal end of the tubular housing, the staple cartridge being adapted for expelling an annular array of staples therefrom, and an anvil assembly including an anvil and an anvil shaft being removably mounted to the distal end portion of the housing. The invention further relates to a shroud, for use with the surgical fastener apparatus, which includes means for demountably attaching the apparatus to the fastener apparatus and means for shielding a predetermined portion of tissue, not intended to be stapled, from entering between a staple cartridge and at least one annular array of buckets or staple forming depressions on an anvil. Optionally, the array of staple forming depressions may be magnetized so as to attract and retain staples expelled from the staple cartridge, but not formed in tissue as a result of the shroud preventing a portion of tissue from being stapled.

The demountable attaching means also comprises a collar adapted for removably mounting the apparatus on the fastening device, which adaptations may include: compressible tabs disposed on an inner wall of the collar to form an interference fit between the collar and the instrument; and a tab and slot configuration, e.g., the inner wall of the collar having at least one slot disposed on it and the instrument having at least one tab for mating with the slot. The collar may further comprise an open portion such that the collar is substantially C-shaped and is adapted for snapping onto the distal end of the tubular housing of the fastening device.

BRIEF DESCRIPTION OF THE DRAWINGS

The foregoing advantages and features of the invention will become more readily apparent and may be understood by referring to the following detailed description of illustrative embodiments of the apparatus for creating partial anastomoses, taken in conjunction with the accompanying drawings, in which:

FIG. 2 illustrates a perspective, broken view of a surgical stapler apparatus according to the invention;

FIG. 2A illustrates a partial view of the staple forming depressions on the anvil;

FIG. 2B illustrates an exploded, partial view of the distal end of the surgical stapler apparatus of FIG. 2;

FIG. 3 illustrates a perspective view of one embodiment of the apparatus for creating a partial anastomosis;

FIG. 4 illustrates a side view of the apparatus of FIG. 3;

FIG. 10 illustrates a partial view of the surgical stapler apparatus positioned in a section of a tubular tissue structure just beyond the anastomotic site;

FIG. 11 illustrates the surgical stapler apparatus of FIG. 9 positioned at the anastomotic site with the purse string suture in place;

DETAILED DESCRIPTION OF THE PREFERRED EMBODIMENTS

Figure 1A:
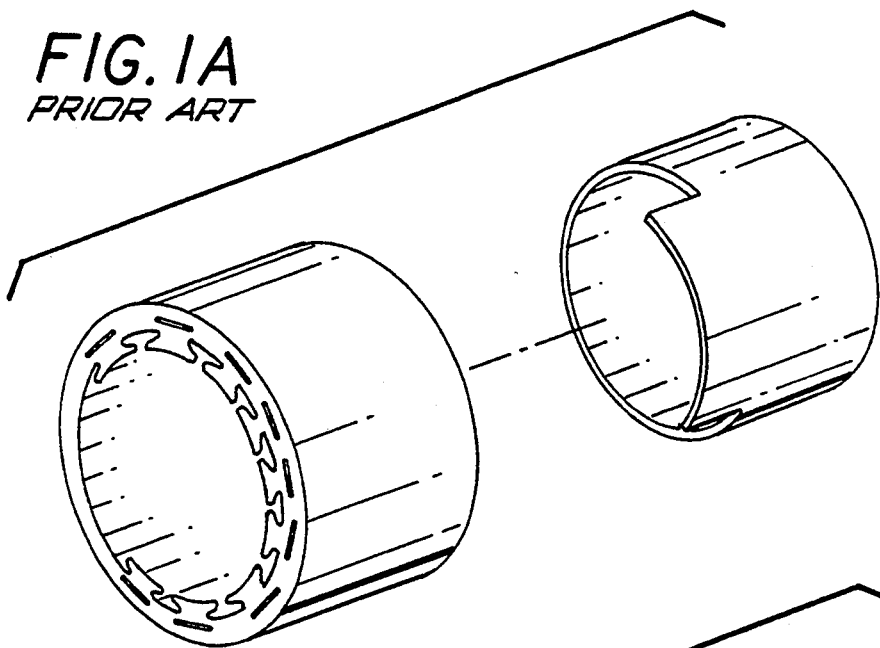
FIG. 1A illustrates one prior art staple array and knife.
Figure 1B:
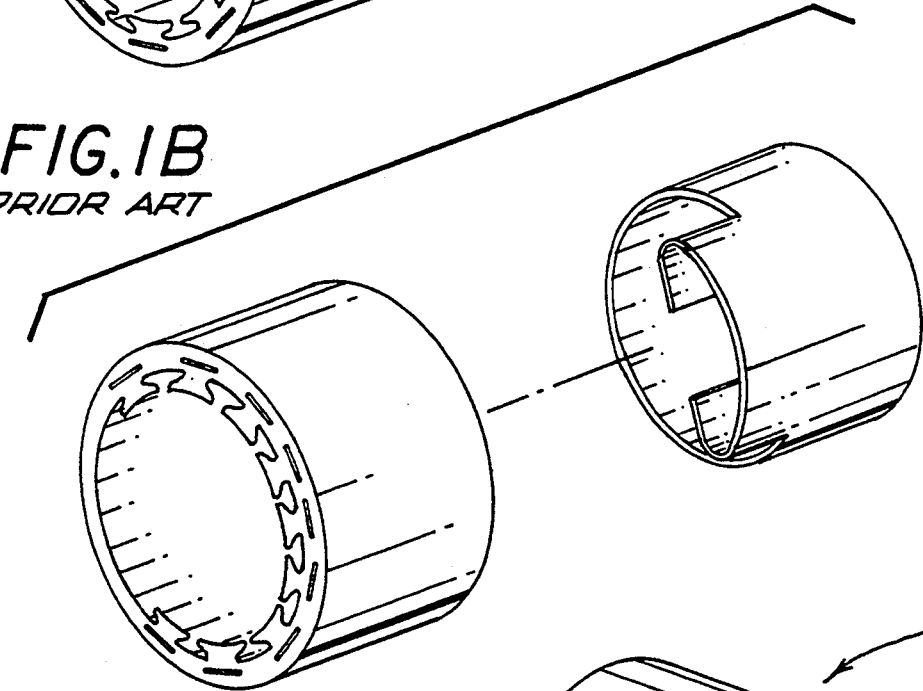
FIG. 1B illustrates another prior art staple array and knife.

Referring now in specific detail to the drawings, in which like references numerals identify similar or identical elements throughout the several views. While the following detailed discussion will focus on specific embodiments for joining together tubular tissue so as to form a less than 360° array of staples, it will be recognized by others having ordinary skill in the art that the device disclosed herein will be useful in other procedures. Heretofore, devices which use a less than 360° staple cartridge and knife combination to create a partial anastomosis are known. Examples of such prior art devices are illustrated in FIGS. 1A and 1B.

FIG. 2 illustrates a surgical stapler apparatus 10, particularly adapted for performing a partial circular anastomosis, i.e., a less than 360° circular staple pattern. Except as noted otherwise, the materials utilized in the components of the apparatus generally include such materials as polycarbonate for housing sections and related components, and stainless steel for components which transmit forces. One preferred polycarbonate material is LEXAN brand polycarbonate available from General Electric company. However, equivalent alternative materials will readily come to the mind of those skilled in the art. Apparatus 10 may be any suitable surgical stapler apparatus, for example, the PREMIUM CEEA TM surgical stapler manufactured by United States Surgical Corporation which is the subject of U.S. patent application Ser. No. 07/702,630 by Green et at., filed May 17, 1991, the disclosure of which is hereby incorporated by reference.

Generally, apparatus 10 includes handle portion 12, and elongated shaft 14 adapted at the distal end portion for releasably receiving anvil shaft 16. The shaft may also be adapted to receive a trocar shaft. In the illustration of FIG. 2, removable anvil 18 is shown detached from anvil shaft 16. Shroud 20 is shown mounted on the distal end of apparatus 10. Collar 22 slides over staple cartridge mounting ring 25 (FIG. 2B) which surrounds annular knife 26. The handle portion 12 of apparatus 10 includes staple pusher actuating handles 28 and 30, safety latch 32 and adjusting wing nut 34.

Referring now to the embodiment of the invention illustrated in FIGS. 2B-5 and initially to FIG. 2B, the distal end of surgical stapler apparatus 10 is shown having shroud 20 mounted about mounting ring 25. Shroud 20 is held in place on apparatus 10 by raised mounting portions 38 biasing against mounting ring 25.

As illustrated in FIGS. 3 and 4, shroud 20 has C-shaped tissue shield 36 extending from collar 22. Raised flexible mounting portions 38 are positioned along inside wall 21 of collar 22 to provide an interference fit between collar 22 and mounting ring 25 when mounted on apparatus 10.

Figure 5:
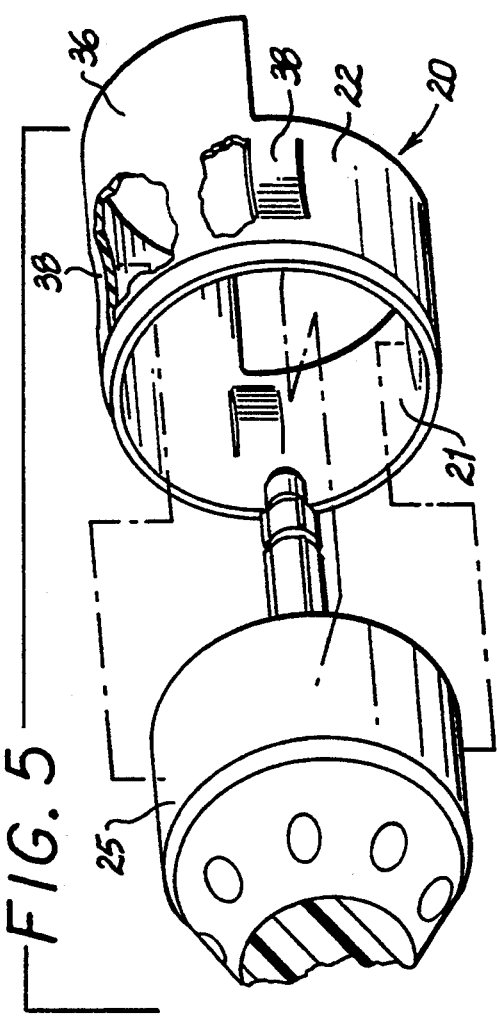
FIG. 5 illustrates a partially cut-away, exploded view of the apparatus of FIG. 3 as it is mounted on the distal end of the surgical stapler apparatus.
Figure 6:
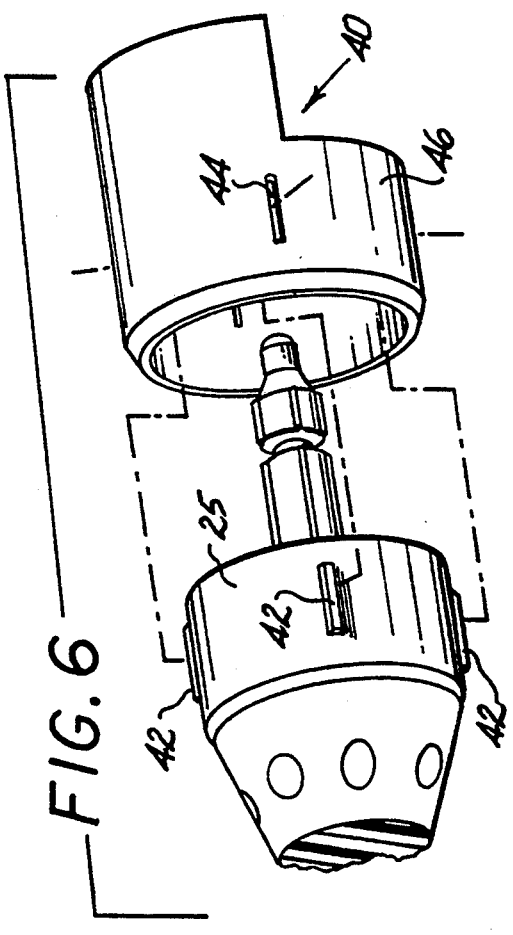
FIG. 6 illustrates an exploded view of another amounting means of the apparatus of the present invention.

Referring now to FIG. 5, shroud 20 is shown in exploded view, separated from apparatus 10. With anvil 18 removed from apparatus 10, shroud 20 is slid onto the distal end of the housing of apparatus 10 over and around mounting ring 25 such that raised mounting portions 38 form an interference or friction fit between inside wall 21 of collar 22 and mounting ring 25. The orientation of shield 36 relative to staple cartridge 24 may be adjusted by the surgeon either before introducing stapling apparatus 10 into the lumen of the tissue to be anastomosed or directly at the site. Maximum flexibility is thereby afforded the surgeon to make necessary adjustments immediately prior to firing the stapler apparatus. This flexibility of having a movably placeable shroud provides the benefit of being able to precisely position a given shroud on the stapler apparatus to achieve the desired degree of anastomosis. It is also within the scope of the present invention to provide shrouds having different degrees of curvature to afford greater flexibility for a surgeon to prevent more or less tissue from being anastomosed.

Figure 9:
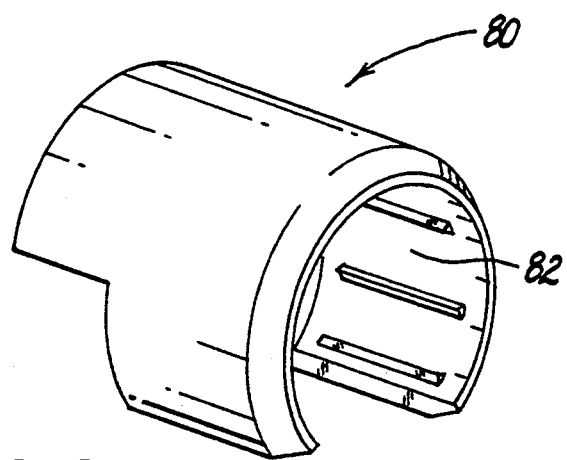
FIG. 9 illustrates a perspective view of yet another mounting means of the apparatus of the present invention.
Figure 8:
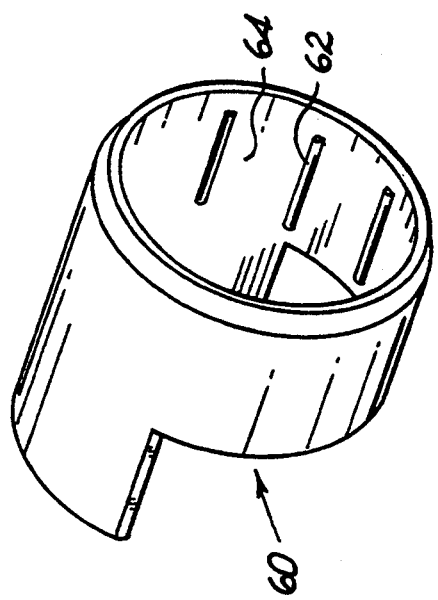
FIG. 8 illustrates a perspective view of another mounting means of the apparatus of the present invention.
Figure 7:
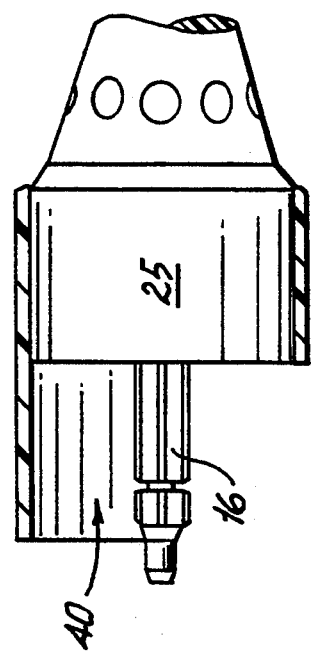
FIG. 7 illustrates a partial cross-section view of the apparatus mounted on the distal end of surgical stapler apparatus.

The general mounting of a typical shroud of the present invention on a stapler apparatus is best illustrated in FIG. 7 which shows the relationship of shroud 40 with respect to mounting ring 25, apparatus 10, and anvil shaft 16. Shroud 40 extends distally so as to cover most of shaft 16 such that when anvil 18 is mounted on shaft 16 staple forming depressions 50 and thus proximal end of anvil are positioned beneath distal end of shroud 40. In this manner tissue will be prevented from becoming caught between proximal end of anvil 18 and distal end of shroud 40. Numerous other mounting methods may be employed some examples of which are illustrated in FIGS. 6-9. For example, in FIG. 6, shroud 40 is shown mounted on mounting ring 25 of apparatus 10 by means of tabs 42 located on the exterior of mounting ring 25 which correspond to slots 44 on collar 46 of shroud 40. In FIG. 8, shroud 60 is shown having mounting tabs 62 distributed longitudinally along interior wall 64 of shroud 60. Tabs 62 are preferably made of compressible material that will permit shroud 60 to be slid over mounting ring 25 on the distal end of apparatus 10 while preventing shroud 60 from sliding freely once mounted on ring 25. FIG. 9 shows another alternative mounting method in which shroud 80 has collar 82 with a less than 360° closure. Shroud 80 is fitted on apparatus 10 by snapping the shroud onto apparatus 10, e.g., by placing shroud 80 adjacent to mounting ring 25 such that the open portion of collar 82 is positioned adjacent to ring 25 and then urging shroud 80 toward mounting ring 25 thereby spreading open portion of collar 82 and fitting same around mounting ring 25. In this mounting alternative it is possible that shroud 80 may be put on apparatus 10 without having to remove anvil 18 before shroud 80 is attached. Alternatively, shroud 80 may be slid over the end of mounting ring 25.

FIGS. 10-13 show the use of shroud 20, by way of example, in an anastomosis procedure. It is to be understood that the other embodiments of the shroud disclosed herein operate in similar fashion. For various anastomosis procedures it may desirable or necessary for the surgeon to retain partial access to the interior of the tissue structure at the anastomotic site after the initial closure is completed. In such instances, anastomosis stapling devices such as the PREMIUM CEEA ™ stapler manufactured by United States Surgical Corporation may be adapted for use with the shroud of the present invention. When surgical stapler apparatus 10 is to be used, for example, in forming a partial anastomosis between two ends 90 and 92 of tubular tissue structure, purse string sutures are placed preferably no more than 2.5 mm from the cut edges of the structures to be anastomosed, to avoid tissue bunching and possible staple malformation. In the event that anvil 18 and shroud 20 have not been previously mounted on the shaft, shroud 20 can be slid over the distal end of the shaft and mounted on the distal end of surgical stapler 10 and anvil 18 can thereafter be slid over the distal end of the shaft and snap-locked in place by means of the spring therein engaging within the recess of the shaft. After passage of the distal end of the apparatus, with shroud 20 mounted thereon, into the structure through a suitable opening, the surgeon manipulates the instrument towards the anastomotic site. Once the instrument is positioned, the surgeon manipulates actuating means for opening the instrument into an extended position until sufficient space is available between cartridge 24 and anvil 18 for the purse string sutures to be tied. The proximal purse string suture is then tied snugly around the center rod to secure the proximal tissue over cartridge 24. With the shroud in place, as the purse string suture is tied about the center rod, the tissue to be kept from being anastomosed is prevented from being tied over cartridge 24. The distal purse string suture is then tied to secure the distal tissue over anvil 18.

Figure 12:
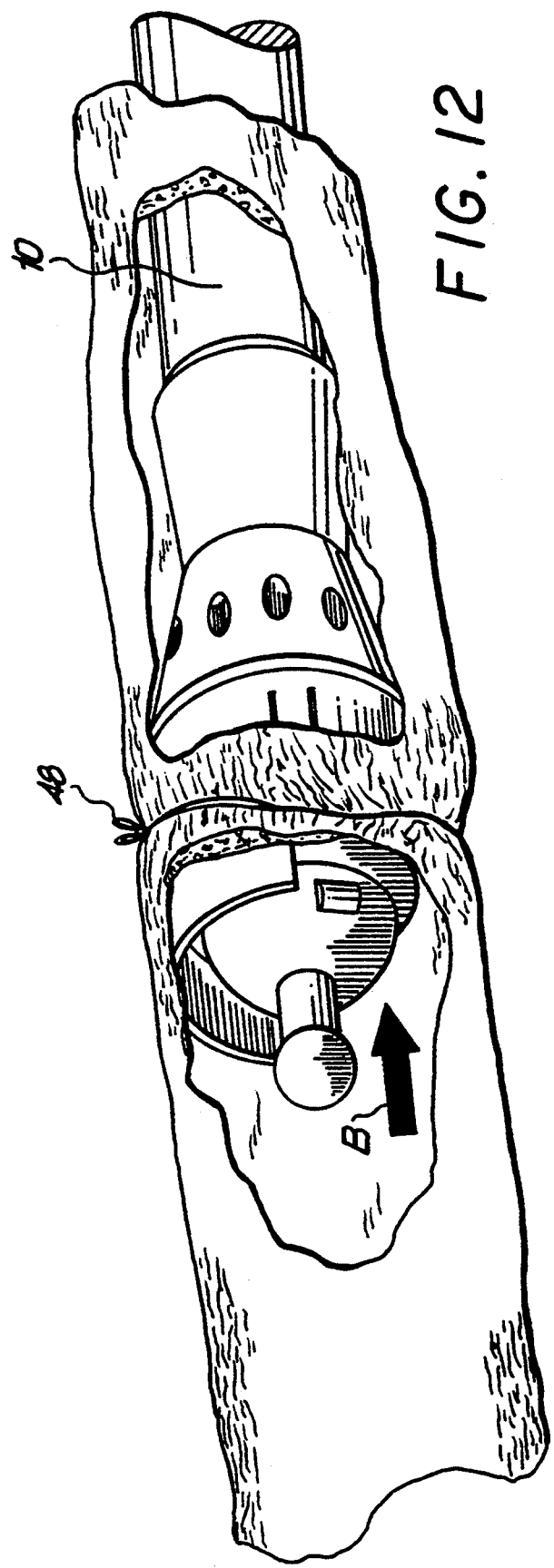
FIG. 12 illustrates the surgical stapler apparatus of FIGS. 10 and 11 during actuation of the instrument as the anvil is pulled towards the staple cartridge assembly and the staples are formed in the tissue.
Figure 13:
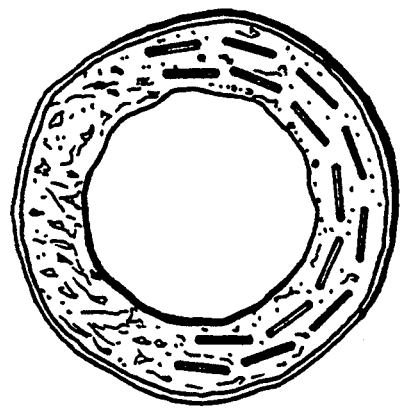
FIG. 13 illustrates a cross-section view of FIG. 12 showing the partial anastomosis of the tubular tissue structure.

Referring to FIG. 11, when purse string suture 48 is drawn snug and tied, the tissue to be anastomosed is drawn in the direction of Arrow A and is positioned between anvil 18 and staple cartridge 24. Tissue which is to remain unstapled is kept out of the staple forming region by C-shaped tissue shield 36. Next, the tissue is approximated by manipulation of the actuating means drawing anvil 18 in the direction of Arrow B, as illustrated in FIG. 12, until anvil 18 and staple cartridge 24 are properly spaced. Staple drivers (not shown) are then activated by squeezing the handles thereby expelling the staples from staple cartridge 24 so that the tissue positioned between anvil staple forming depressions 50 (FIG. 2A) and the staple cartridge, is stapled. Staple forming depressions 50 are preferably magnetized so as to attract and retain staples expelled from staple cartridge 24 but not formed in the tissue. Alternatively, the surgeon may remove the desired amount of staples from cartridge 24 to correspond with the size shroud being used. As illustrated in FIG. 13, upon actuation of apparatus 10, a partial, i.e., less than 360° anastomosis is achieved.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A circular anastomosis fastening apparatus comprising: p1 an elongated housing;
    a staple cartridge mounted at a distal end of said elongated housing; and
    shroud means detachably mounted adjacent to said staple cartridge for shielding a predetermined portion of tissue from being engaged by said staple cartridge, wherein upon actuation of the circular anastomosis fastening device, a full circular anastomosis is prevented and a partial anastomosis is created.

2. An apparatus according to claim 1, wherein said shroud means includes attaching means incorporated in said proximal end of said shroud means.

3. An apparatus according to claim 1, wherein said shroud means further comprises a C-shaped portion incorporated in said distal end extending longitudinally away from an attaching means whereby upon drawing together of a purse string suture formed near an end of the tissue to be anastomosed, a predetermined portion of tissue is shielded from being engaged by said staple cartridge.

4. An apparatus according to claim 1, wherein said shroud means includes an attaching means having a collar portion adapted for removably mounting said shroud means adjacent to said staple cartridge.

5. An apparatus according to claim 4, wherein said collar portion comprises a wall having an inner surface and an outer surface, said collar portion further comprising means disposed on said inner surface for engaging said elongated housing.

6. An apparatus according to claim 5, wherein said engaging means includes at least one compressible raised portion.

7. An apparatus according to claim 5, wherein said engaging means includes at least one slot adapted for mating with at least one tab on said elongated housing.

8. An apparatus according to claim 4, wherein said collar portion is substantially C-shaped having an open portion adapted for snapping said collar portion onto said elongated housing.

9. A surgical stapler apparatus comprising:
    a tubular housing having proximal and distal end portions;
    a staple cartridge mounted in said distal end portion of said housing adapted for expelling an annular array of staples therefrom;
    an anvil assembly connected to said distal end portion of said housing, said anvil assembly including an anvil and an anvil shaft, said anvil shaft received within said tubular housing, said anvil including at least one annular array of buckets configured to form said staples;
    means mounted on said housing for shielding a predetermined portion of tissue from entering between said staple cartridge and said at least one annular array of buckets on said anvil assembly wherein upon actuation of the surgical stapler apparatus, a full anastomosis is prevented and a partial anastomosis is created.

10. An apparatus according to claim 9, wherein said shielding means is detachably mounted on said housing.

11. A surgical stapler apparatus according to claim 9, further comprising means for retaining loose staples discharged from said staple cartridge.

12. A surgical stapler apparatus according to claim 11, wherein said staple retaining means includes at least one magnetized portion of said stapler apparatus.

13. A surgical stapler apparatus according to claim 11, wherein said staple retaining means includes said at least one annular array of buckets being magnetized.

14. A surgical stapler apparatus according to claim 9, wherein said tissue shielding means further comprises a shroud detachably mounted on said distal end of said tubular housing.

15. A surgical stapler apparatus according to claim 14, wherein said shroud further comprises:
 a collar portion adapted for detachably mounting said shroud adjacent to said distal end of said tubular housing; and
 a C-shaped portion extending longitudinally from said collar portion for shielding a predetermined portion of tissue from entering between said staple cartridge and said at least one annular array of buckets on said anvil assembly.

16. A surgical stapler apparatus according to claim 15, wherein said collar portion comprises a wall having an inner surface and an outer surface, said collar portion further comprising means disposed on said inner surface for engaging said tubular housing.

17. A surgical stapler apparatus according to claim 16, wherein said engaging means includes at least one compressible raised portion.

18. A surgical stapler apparatus according to claim 16, wherein said engaging means includes at least one slot adapted for mating with at least one tab on said tubular housing.

19. A surgical stapler apparatus according to claim 15, wherein said collar portion is substantially C-shaped having an open portion adapted for snapping said collar portion onto said tubular housing.

20. A surgical stapler apparatus comprising:
 a tubular housing;
 a shaft extending from said tubular housing;
 a fastener cartridge for holding an array of fasteners;
 an anvil assembly adapted to be removably connected to said shaft, said anvil assembly having an array of staple forming depressions;
 means for moving one of said anvil assembly and said cartridge assembly from a first spaced apart position to a second position to grasp a tissue portion therebetween; and
 means for blocking penetration of tissue in a region between said cartridge and said anvil assembly wherein upon actuation of said surgical stapler apparatus, a full anastomosis is prevented and a partial anastomosis is created.

21. An apparatus according to claim 20, wherein said blocking means comprises a member mounted on said tubular housing.

22. A surgical stapler apparatus according to claim 21, wherein said member further comprises a shroud detachably mounted on a distal end of said tubular housing.

23. A surgical stapler apparatus according to claim 22, wherein said shroud further comprises a collar portion for detachably mounting said shroud on said distal end of said tubular housing and a C-shaped portion extending longitudinally from said collar portion for shielding a predetermined portion of tissue from entering between said staple cartridge and said array of staple forming depressions on said anvil assembly.

* * * * *